US008792700B2

(12) United States Patent
Riddell et al.

(10) Patent No.: US 8,792,700 B2
(45) Date of Patent: Jul. 29, 2014

(54) TOMOGRAPHIC RECONSTRUCTION OF A MOVING OBJECT

(75) Inventors: Cyril Riddell, Issy-les-Moulineaux (FR); Lorenzo Audibert, Saint Mandé (FR)

(73) Assignee: General Electric Company, Schenectady, NY (US)

( * ) Notice: Subject to any disclaimer, the term of this patent is extended or adjusted under 35 U.S.C. 154(b) by 469 days.

(21) Appl. No.: 13/250,245

(22) Filed: Sep. 30, 2011

(65) Prior Publication Data

US 2012/0114207 A1    May 10, 2012

(30) Foreign Application Priority Data

Oct. 1, 2010    (FR) ...................................... 10 57978

(51) Int. Cl.
*G06K 9/00*    (2006.01)
(52) U.S. Cl.
USPC ............................. 382/131; 382/132; 382/275
(58) Field of Classification Search
CPC ................ G06T 11/003; G06T 11/005; G06T 2211/424; A61B 6/5258; A61B 6/5264
USPC .......................................... 382/131, 132, 275
See application file for complete search history.

(56) References Cited

U.S. PATENT DOCUMENTS

| | | | | |
|---|---|---|---|---|
| 8,310,233 | B2 * | 11/2012 | Trzasko et al. ................. | 324/309 |
| 8,326,054 | B2 * | 12/2012 | Chen et al. ..................... | 382/232 |
| 2011/0282181 | A1 * | 11/2011 | Wang et al. ................... | 600/407 |

OTHER PUBLICATIONS

Donoho, David L. "Compressed Sensing." IEEE Transactions on Information Theory. 52.4 (2006): 1289-1306. Print.*
Compressive Sampling, E. Candès, Proceedings of the International Congress of Mathematicians, Madrid, Spain, 2006 © 2006 European Mathematical Society.
Robust uncertainty principles: Exact signal reconstruction from highly incomplete frequency information, E. Candès, J. Romberg and T. Tao, IEEE Transactions on Information Theory in Information Theory Feb. 2006.
Prior image constrained compressed sensing (PICCS): a method to accurately reconstruct dynamic CT images from highly undersampled projection data sets, G. Chen, J. Tang and S. Leng, Medical Physics 2008.
L. Daubechies, M. Defrise, and C. De Mol, "An iterative thresholding algorithm for linear inverse problems with sparsity constraint.", Communications on Pure and Applied Mathematics, vol. 57, No. 11, pp. 1413-1457, 2004.
A. Beck and M. Teboulle, "A fast iterative shrinkage-thresholding algorithm for linear inverse problems" SIAM Journal on Imaging Science, vol. 2, No. 1, pp. 183-202, 2009.

(Continued)

*Primary Examiner* — Michael A Newman
(74) *Attorney, Agent, or Firm* — Global Patent Operation (57) ABSTRACT

A method is provided for processing a sequence of sets of 2D projection images of a moving object, wherein the sequence of sets of 2D projection images is obtained by a medical imaging system that is in motion along a trajectory. The method comprises determining a sequence of images which minimize a function dependant on a set of 3D images, a term of fidelity of the sequence of images, a function of spatial and temporal compression of the sequence of images, a compressibility parameter, and a sequence of operators for an approximate modelling of motion. The sequence of operators leads to a compression constraint augmented by partial knowledge of the motion and the minimization comprises defining a decreasing sequence of degrees of compressibility for which an estimation is determined from an initial sequence.

7 Claims, 4 Drawing Sheets

(56) References Cited

OTHER PUBLICATIONS

L.I. Rudin, S. J. Osher, and E. Fatemi, "Non linear total variation based noise removal algorithms", Phys. D, vol. 60, pp. 259-268, 1992.

Seung-Jean Kim, K. Koh, M. Lustig, Stephen Boyd and Dimitry Gorinevsky, "An Interior point method for large-scale l1-regularized least squares" IEEE signal processing, vol. 1, No. 4, 1932-4553, 2007.

T. Chan, S.Osher and J. Shen, The digital Tv filter and nonlinear denoising, IEEE Transactions on Image Processing, vol. 10, issue 2, pp. 231-241.

Blondel, C., et al. "Reconstruction of Coronary Arteries from a Single Rotational X-Ray Projection Sequence", IEEE Transactions on Medical Imaging, vol. 25, No. 5, May 1, 2006, pp. 653-663.

Hansis, Eberhard, et al. "High-quality 3-D Coronary Artery Imaging on an Interventional C-arm X-Ray System", Medical Physics, vol. 37, No. 4, Mar. 17, 2010, pp. 1601-1609.

Chen, Guan-Hong, et al. "Prior Image Constrained Compressed Sensing (PICCS): A method to Accurately Reconstruct Dynamic CT Images from Highly Undersampled Projection Data Sets", Medical Physics, vol. 35, No. 2, Jan. 28, 2008, pp. 660-663.

Frank Bergner, Timo Berkus, markus Oelhafen, Patrik Kunz, Tinsu Pan, Rainer Grimmer, Ludwig Ritschl, Marc Kachelriess, "An Investigation of 4D cone-beam CT algorithms for slowlyrotating scanners", Medical Physics, vol. 37, No. 9, Sep. 2010, pp. 5044-5053.

Cyril Riddell, et al. "Frequency Weighted Least Squares Reconstruction of Truncated Transmission SPECT Data", Transactions on Nuclear Science, vol. 43, No. 4, Aug. 1, 1996, pp. 2292-2298.

Thibault, Jean-Baptiste, et al. A three-dimensional statistical approach to improved image quality for multislice helical CT, Medical Physics, vol. 34, No. 11, Oct. 29, 2007, pp. 4526-4544.

Manya V Afonso, et al. "Fast Image Recovery Using Variable Splitting and Constrained Optimization", vol. 18, No. 9, Sep. 1, 2010, pp. 2345-2356.

Beck, A. et al. "Fast Gradient-Based Algorithms for Constrained Total Variation Image Denoising and Deblurring Problems", vol. 18, No. 11, Nov. 1, 2009, pp. 2419-2434.

Lu X, et al. "Adaptive wavelet-Galerkin methods for limited angle tomography", Image and Vision Computing, vol. 28, No. 4, Apr. 1, 2010, pp. 696-703.

Emil Y Sidky, et al. "Effect of the data constraint on few-view, fan-beam CT image reconstruction by TV minimization", Nuclear Science Symposium Conference Record, Oct. 1, 2006, pp. 2296-2298.

Yu K-K R, et al. "Limited angle tomography using regularized extrapolation technique", Speech,, Image Processing and Neural Networks, 1994. Proceedings, Issip NN '94., 1994 International Symposium on, Apr. 13, 1994, pp. 413-416.

Singh V, et al. "Limited view CT reconstruction and segmentation via constrained metric labeling" Computer Vision and Image Understanding, vol. 112, No. 1, Oct. 1, 2008, pp. 67-80.

Sami, Sebastian Brandt, et al. "Structure-From-Motion Without Correspondence From Tomographic Projections by Baysian Inversion Theory", IEEE Transaction on Medical Inaging, vol. 26, No. 2, Feb. 1, 2007, pp. 238-248.

Ofri Sadowsky, et al. "Deformable 2D-3D Registration of the Pelvis with a Limited Field of View, Using Shape Statistics", Oct. 29, 2007, Medical Image Computing and Computer-Assisted in Intervention A Miccai 2007, pp. 519-526.

La Rivi GBP Ere P J, et al. "Few-View Tomography Using Roughness-Penalized Nonparametric Regression and Periodic Spline Interpolation", IEEE Transactions on Nuclear Science, vol. 46, No. 4, Aug. 1, 1999, pp. 1121-1128.

French Search Report and Written Opinion issued on Jun. 21, 2011 in connection FR Patent Application 1057978 filed on Oct. 1, 2010.

\* cited by examiner

TOMOGRAPHIC RECONSTRUCTION OF A MOVING OBJECT

BACKGROUND OF THE INVENTION

1. Field of the Invention

In general, the field of the invention concerns tomographic reconstruction and more particularly the reconstruction of a sequence of 3D image(s) describing a moving object to be imaged.

2. Description of Related Art

Figure 1:
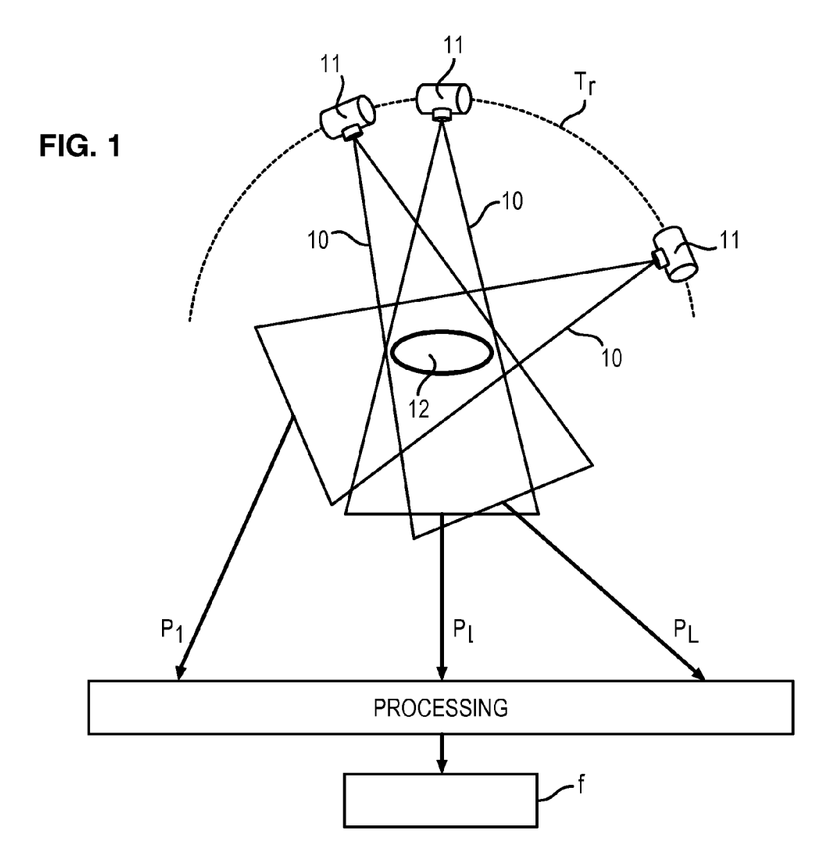
FIG. 1 schematically illustrates the acquisition of 2D images of an object such as an organ.

Tomography allows images of an object to be obtained in the form of slices of a region of interest, by acquiring projections. FIG. 1 schematically illustrates the acquisition of 2D images of an object such as an organ, and the tomographic reconstruction of a 3D image of this organ. The reconstruction of a 3D image by tomography comprises the emission of X-rays 10 from a source towards the organ 12, the X-rays being emitted at different angles l∈{1, ..., L} which define the trajectory Tr of the source (commonly an angle of rotation). After passing through the organ 12, the X-rays 10 are detected by a detector (not illustrated) to form a set of 2D projections. There are as many 2D projections acquired as angles under consideration (i.e. L acquisitions). Acquisition is initiated by the detector, which is located facing the X-ray source 11, e.g. a digital camera.

One application of tomography is the detection and characterization of a body lesion e.g. stenosis of a patient's vessel. The acquired 2D projections are used to reconstruct a 3D image of the object. This 3D image is more precisely a 3D mapping of the X-ray attenuation coefficients of the exposed medium. It is by means of this mapping that a radiologist practitioner interprets this image in relation to observed differences in contrast.

An iterative 3D reconstruction method is known. This method is based on a discrete matrix expression of the tomographic reconstruction problem. The method is implemented in a processing unit of a medical imaging system. More precisely, the problem is modelled by the following equation:

$$Rf = p$$

where p is the vector of the L acquired projections, R is a projection operator which models the tomographic imaging system and its trajectory for acquisition of the L projections p, and f is the 3D image of the object to be reconstructed. The tomographic reconstruction problem is to determine f having knowledge of p and R.

One known solution to the above-mentioned equation is the solving of the following criterion:

$$\begin{cases} Q(g) = \frac{1}{2}\|Rg - p\|_2^2 \\ g^* = \underset{g}{\operatorname{argmin}} Q(g) \end{cases}$$

where $\|\ \|_2$ symbolizes the Euclidian norm called $L_2$. Minimization of the criterion $Q(g)$ relative to $g$ gives good results ($g^* \approx f$) when the set of projections $p$ is such that L is large (typically several hundred) and when the set of L angles covers at least 180°. These conditions are commonly verified when the organ is static during the time needed to perform a rotation of the imaging system.

A problem arises when the organ is in motion and is therefore represented by a series of 3D images $\vec{f} = \{f(t_1), \ldots, f(t_N)\}$ where $f(t_n)$ represents the object at the position referenced $t_n$.

The set of projections p is interpreted as a sequence of sets of projections $\vec{p} = \{p(t_1), \ldots, p(t_N)\}$ where each $p(t_n)$ contains the angles available when the object is in the position referenced $t_n$. With a single rotation of the system, the reconstruction of $f(t_n)$ is degraded.

If the motion is ignored, and reconstruction is performed by minimizing the criterion Q(g), the solution obtained is:

$$g^* = \underset{g}{\operatorname{argmin}} Q(g) = \sum_{n=1}^{N} f(t_n)$$

It is degraded by object motion which is averaged on the reconstruction. The modelling of the trajectory of the system reduced to the angles of the projections $p(t_n)$ is denoted $R(t_n)$. The 3D image reconstructed from:

$$\begin{cases} Q(g, t_n) = \frac{1}{2}\|R(t_n)g - p(t_n)\|_2^2 \\ g^*(t_n) = \underset{g}{\operatorname{argmin}} Q(g, t_n) \end{cases}$$

is degraded since $R(t_n)$ differs from R in that the number of projections of $R(t_n)$, lower than L, is too small and in that the angle coverage is potentially less than 180° C. The sampling condition therefore requires that each $p(t_n)$ contains L projections and covers 180° C. It can then be seen that $\vec{p}$ must contain N×L projections. Yet, such acquisition cannot be envisaged since it implies multiplying N times the X-ray dose (and optionally the quantity of contrast product) and additionally it lasts N times longer.

One alternative consists of integrating the motion of the object by means of a sequence of operators $M = \{M(t_1), \ldots, M(t_N)\}$ which exactly models object motion i.e. such that:

$$\forall n, M(t_n)f(t_n) = f(t_{ref})$$

where $f(t_{ref})$ is the 3D image of the object at a reference position. Reconstruction is then obtained by minimizing the criterion:

$$\begin{cases} Q(g, M, t_n) = \frac{1}{2}\|R(t_n)M^{-1}(t_n)g - p(t_n)\|_2^2 \\ g^*(t_{ref}) = \underset{g}{\operatorname{argmin}} \sum_{n=1}^{N} Q(g, M, t_n) \end{cases}$$

so that the complete sequence $\vec{p} = \{p(t_1), \ldots, p(t_N)\}$ is used to obtain a single image $g^*(t_{ref})$ from which each position $g^*(t_n) = M^{-1}(t_n)g^*(t_{ref})$ can be inferred. However, knowledge of M is most often only approximate or only valid in a restricted part of the image. For example, in the document [Blondel C, Malandain G, Vaillant R, Ayache N., "*Reconstruction of coronary arteries from a single rotational X-ray projection sequence*" IEEE Trans. Med. Imaging 25(5):653-63], the motion of the coronaries is estimated in the projected images and integrated in the reconstruction. However, only the image of the coronaries is obtained, all the other structures being removed from the projective images by pre-processing.

Alternatively, reconstruction is obtained independently for each position $t_n$ by minimizing the criterion:

$$\begin{cases} S(g) = \|W_{xyz}g\|_1 \\ g^*(t_n, \lambda) = \underset{g}{\operatorname{argmin}}\{\lambda S(g) + Q(g, t_n)\} \end{cases}$$

where $\|\ \|_1$ is the so-called $L_1$ norm, $W_{xyz}$ is a spatial transformation enabling the individual compression of the 3D images (e.g. wavelets, gradient, identity (denoted Id . . . ) and $\lambda$ is a prior fixed scalar. These compressed images have not yet given any convincing results for clinical application. It is on reconstructing solely the coronary vessels, after removing all other information from the projections by pre-processing [Hansis E, Carrol Schäfer D, Dössel O, Grass M., "*High Quality 3-D coronary artery imaging on an interventional C-arm X-ray system*" Med Phys. 37(4):1601-9] that the criterion $W_{xyz}$=Id is known to produce a sparse image of the coronaries i.e. equal to 0 in all the pixels except the vessels whose volume is known to be very restricted (a few percent in the 3D image).

In the document [Chen G H, Tang J, Leng S., "*Prior image constrained compressed sensing (PICCS): a method to accurately reconstruct dynamic CT images from highly undersampled projection data sets*" Med. Phys. 35(2): 660-3] it is shown that it is possible to avoid the pre-processing of projection images, provided a strong assumption is made of prior image knowledge denoted $f_p$, close to the solution. The constraint $S(g)$ is then replaced by $\alpha S(g)+(1-\alpha)S(g-f_p)$ where $0 \leq \alpha < 1$. Variants of the cited techniques are compared in the document [Bergner F, Berkus T, Oelhafe M, Kunz P, Pan T, Grimmer R, Ritschl L, Kachelrieß M, <<*An investigation of 4D cone-beam CT algorithms for slowly rotating scanners*>> Med. Phys. 37(9): 5044-53].

BRIEF SUMMARY OF THE INVENTION

One objective of the invention is to obtain a 3D reconstruction of a moving object, represented by a series of 3D images $\vec{f}=\{f(t_1), \ldots, f(t_N)\}$ from a sequence of 2D projection images $\vec{p}=\{p(t_1), \ldots, p(t_N)\}$ obtained with a medical imaging system.

The prior art shows that there exist reconstruction algorithms allowing the generation of compression approximations of a 3D image of an object. These reconstructions are obtained by minimizing a criterion of the form $$g^*(\lambda) = \underset{g}{\operatorname{argmin}}\{\lambda S(g) + Q(g)\}$$

where $Q(g)$ models the relationships between the solution and measurement data, $S(g)$ imposes the type of compressibility of the approximate solution, whereas the degree of compressibility is fixed a priori as being proportional to the scalar $\lambda$. That in general, the solution $g^*(\lambda)$ is not unique and depends upon the starting point of the minimization procedure. That in general there exists an approximation error $g^*(\lambda)-f$, itself proportional to $\lambda$ (it will be said that the solution is biased, however this bias is not uniform on the solution). In addition, that in general it is not possible to have exact prior knowledge of the motion $M=\{M(t_1), \ldots, M(t_N)\}$ of the object, but on the other hand it is frequent to have partial prior information on the motion.

A first aspect of the invention is a method for processing a sequence of sets of 2D projection images of a moving object. The motion of which is described by a set of positions referenced by $t=\{t_1, \ldots, t_N\}$ wherein the sequence of sets of 2D projection images is obtained by a medical imaging system that is in motion along a trajectory. The method comprises determining a sequence of images which minimize a function dependant on a set of 3D images, a term of fidelity of the sequence of images, a function of spatial and temporal compression of the sequence of images, a compressibility parameter, and a sequence of operators for an approximate modelling of motion. The sequence of operators leads to a compression constraint augmented by partial knowledge of the motion. Minimization comprises defining a decreasing sequence of degrees of compressibility for which, an estimation is determined from an initial sequence.

A second aspect of the invention is a medical imaging system comprising an acquisition unit. The acquisition unit comprises a radiation source and a sensor. The acquisition unit is configured to acquire a sequence of sets of 2D projection images of a moving object while the acquisition unit is in motion along a trajectory, wherein the motion of the moving object is described by a set of positions. The medical imaging system further comprises a computing unit configured to determine a sequence of images which minimizes a function a function dependant on a set of 3D images, a term of fidelity of the sequence of images, a function of spatial and temporal compression of the sequence of images, a compressibility parameter, and a sequence of operators for an approximate modelling of motion.

BRIEF DESCRIPTION OF THE SEVERAL VIEWS OF THE DRAWINGS

The accompanying drawings, which are incorporated in and constitute a part of the specification, illustrate one or more embodiments and, together with the description, explain these embodiments. In the drawings.

DETAILED DESCRIPTION OF THE INVENTION

Figure 2:
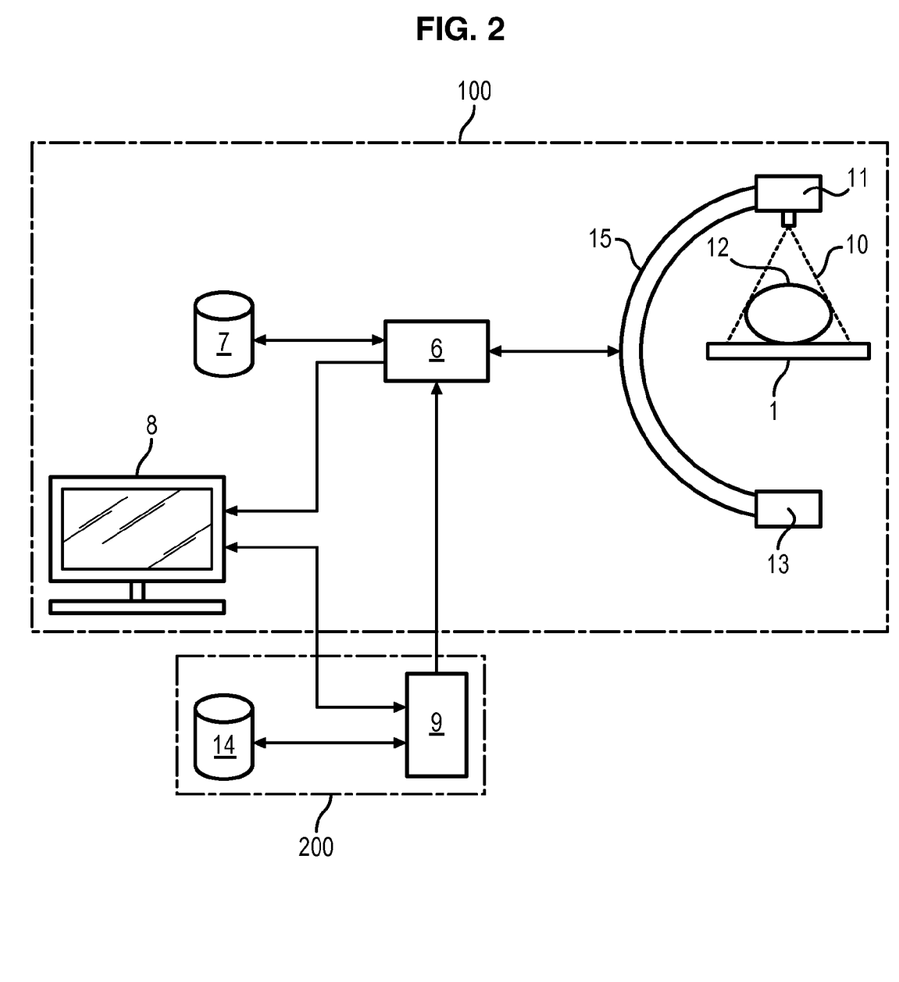
FIG. 2 schematically illustrates a medical imaging system according to an embodiment of the invention.

FIG. 2 schematically illustrates a medical imaging system 100 to acquire 2D projection images for the reconstruction of a 3D image of an object such as an organ. The system may be used for the detection and characterization of stenosis in vessels. The medical imaging system 100 comprises: a support 1 intended to receive a patient (not illustrated) to be examined, in whom it is desired to image an organ 12; a source 11 intended to emit an X-ray beam 10; a detector 13 arranged facing the source 11 and configured to detect the X-rays emitted by the) source 11; a control unit 6; a storage unit 7; and a display unit 8. The X-ray source 11 and the detector 13 are connected by means of a C-arm 15, for example.

The detector 13 may be a semiconductor image sensor, for example comprising caesium iodide phosphor (scintillator) on a transistor/amorphous silicon photodiode array. Other suitable detectors are: a CCD sensor or a direct digital detector which directly converts X-rays into digital signals. The detector 13 illustrated in FIG. 2 is planar and defines a planar image surface, however, other geometries are evidently also suitable.

The control unit 6 is used to control an acquisition by setting several parameters such as the radiation dose to be emitted by the X-ray source and the positioning of the source 11 and detector 13. It is connected to the C-arm 15 via a wire or wireless connection. The control unit 6 may comprise a reader device (not illustrated) e.g. a diskette reader, CD-ROM, DVD-ROM reader or connection ports to read the instructions of the processing method from an instruction medium (not shown) e.g. a diskette, CD-ROM, DVD-ROM, USB key or more generally any removable memory medium or via a network connection.

The storage unit 7 is connected to the control unit 6 to record parameters and acquired images. It is possible to place the storage unit 7 either inside or outside the control unit 6. The storage unit 7 may be formed of a hard disk or SSD, or any other removable, re-write storage means (USB keys, memory cards etc. . . . ). The storage unit 7 may be a ROM/RAM memory of the control unit 6, a USB key, memory card or memory of a central server.

The display unit 8 is connected to the control unit 6 to display acquired images and/or information on acquisition control parameters. For example, the display unit 8 may be a computer screen, a monitor, flat screen, plasma screen or any other type of known display device. The display unit 8 allows the practitioner to control the reconstruction and/or display of acquired 2D images.

The medical imaging system 100 is coupled with a processing system 200. The processing system 200 comprises a computing unit 9 and storage unit 14. The processing system 200 receives acquired images stored in the storage unit 7 of the medical imaging system 100 from which it performs a certain number of processing operations (see below) e.g. a reconstruction of a 3D image from 2D images. The transmission of data from the storage unit 7 of the medical imaging system 100 towards the computing unit 9 of the processing system 200 may take place via an internal or external computer network or using any suitable physical memory medium e.g. diskettes, CD-ROM, DVD-ROM, external hard disk, USB key, SD card etc. . . .

The computing unit 9 is one or more computers for example, or one or more processors, one or more microcontrollers, one or more microcomputers, one or more programmable logic controllers, one or more application-specific integrated circuits, other programmable circuits, or other devices which include a computer such as a workstation. As a variant, the computer 9 may comprise a reader device (not illustrated) for example a diskette reader, CD-ROM or DVD-ROM reader, or connection ports to read the instructions of the processing method from an instruction medium (not illustrated) e.g. a diskette, CD-ROM, DVD-ROM, or USB key or more generally any removable memory medium or via a network connection. In addition, the processing system 200 comprises a storage unit 14 to store data generated by the computing unit 9.

The computing unit 9 may be connected to the display unit 8 (as in FIG. 2) or to another display unit (not illustrated). In addition, the processing unit 200 can be included in the medical imaging system 100, their respective storage units 6,7 in this case being merged.

The method for processing images is implemented, for example, in the processing unit 6 of the medical imaging system 100 illustrated in FIG. 2. The method for processing images allows the reconstruction of a sequence of 3D images $\vec{f}=\{f(t_1), \ldots, f(t_N)\}$ representing a moving object for a set of positions referenced by $t=\{t_1, \ldots, t_N\}$. For each position, there is a set of 2D projection images $p(t_n)$ obtained by means of the medical imaging system moving along a trajectory around the moving object (with the trajectory commonly being an angle of rotation).

Figure 3:
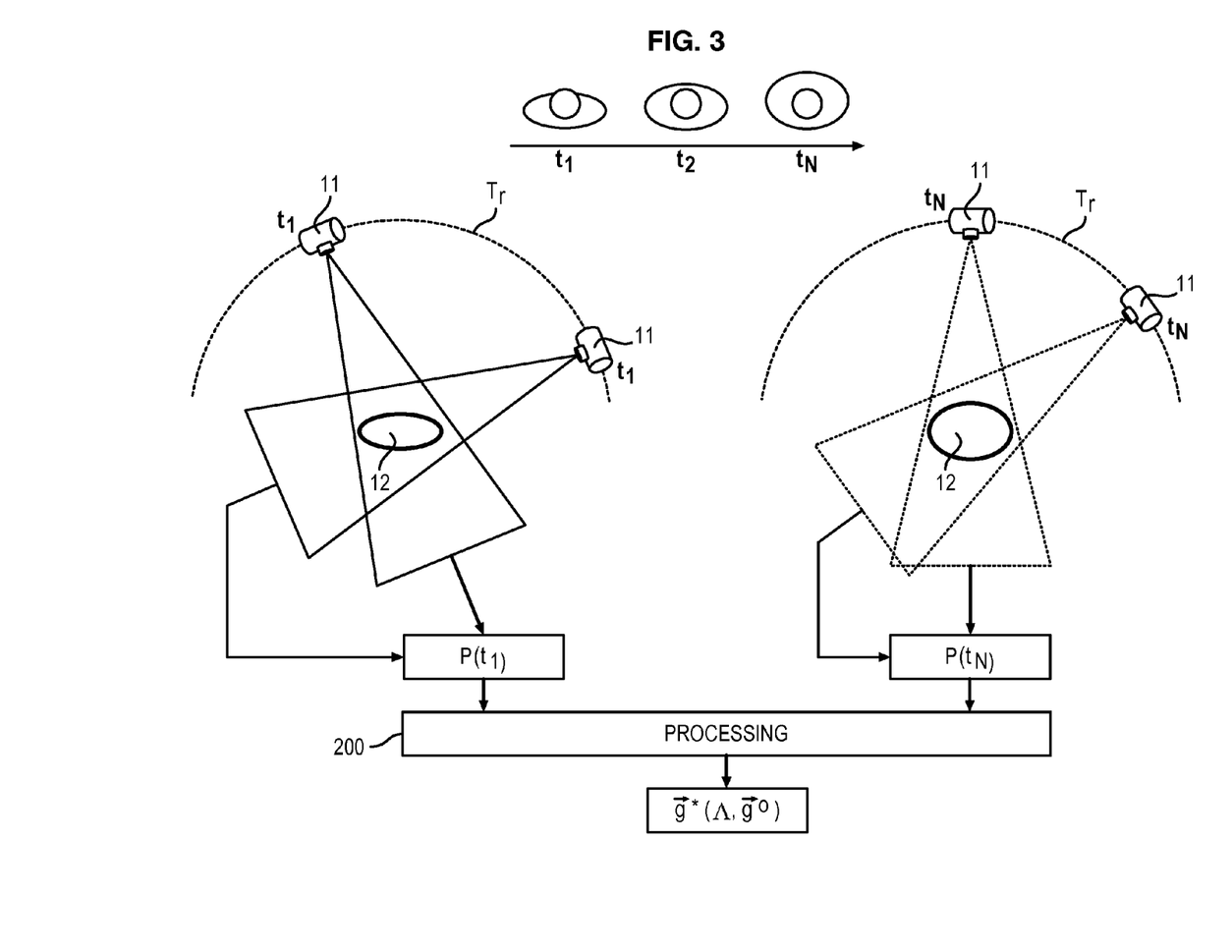
FIG. 3 is a flow diagram of a method according to an embodiment of the invention.

FIG. 3 illustrates the acquisition of sets of 2D projection images $p(t_n)$ for different positions $t_n$ of the (moving) object 12. For each instant $t_n$ of the motion, there is a corresponding set of 2D projection images $p(t_n)$. The sets of 2D projection images $p(t_n)$ may be previously acquired, for example, and retrieved from the storage unit 14 of the processing unit 200 or from the storage unit 7 of the medical imaging system 100, and processing of the 2D projection images is performed in the computer 9 of the processing unit 200. Each set of 2D projection images $p(t_n)$ is such that $R(t_n)f(t_n)=p(t_n)$ where $R=\{R(t_1), \ldots, R(t_N)\}$ is the sequence of the projection operators which model the sampling made by the medical imaging system for each position $t_n$ of the object while the system is in movement.

For each position $t_n$ of the object, the following least-squares function is defined:

$$Q(g, t_n) = \frac{1}{2}\|R(t_n)g - p(t_n)\|_2^2$$

and the associated composite function:

$$Q(\vec{g}) = \frac{1}{2}\sum_{n=1}^{N}\|R(t_n)g(t_n) - p(t_n)\|_2^2.$$

Minimization relative to $\vec{g}$ of $Q(\vec{g})$ allows reconstruction of a sequence of 3D images $\vec{g}=\{g^*(t_1), \ldots, g^*(t_N)\}$ of all the positions of the object, in which each 3D image $g^*(t_n)$ is considerably degraded by the reduced number of projection images contained in each sequence of images $p(t_n)$. For example, in the document [Riddell C, Savi A, Gilardi M C, Fazio F, *"Frequency weighted least squares reconstruction of truncated transmission SPECT data."* IEEE Trans. Nucl. Sci. 43(4):2292-8] and [Thibault J B, Sauer K D, Bouman C A, Hsieh J., *"A three-dimensional statistical approach to improved image quality for multislice helical CT"*. Med Phys. 34(11):4526-44] or alternative, weighted least-squares functions can be found to the above equations.

In addition, a function of spatial and temporal compression of the image sequences is defined as follows:

$$S(\vec{g})=\|\mathfrak{I}_t W_{xyz}\vec{g}\|_1$$

where $W_{xyz}\vec{g}=\{W_{xyz}g(t_1), \ldots, W_{xyz}g(t_N)\}$ and is a spatial transform enabling individual compression of the 3D images (e.g. wavelets, gradient, identity, . . . ) and $\mathfrak{I}_t$ is a transform (e.g. derived from Fourier analysis) along the axis t followed by the motion.

It is assumed that there is prior knowledge of a sequence of operators $M=\{M(t_1), \ldots, M(t_N)\}$ for approximate modelling of motion allowing the construction of an augmented compression constraint such as $S(M\vec{f})\leq S(\vec{f})$ where $M\vec{f}=\{M(t_1)f(t_1), \ldots, M(t_N)f(t_N)\}$ and $\vec{f}$ is the solution to the fully sampled problem of tomographic reconstruction.

The integration of measurements and of the compressibility assumption augmented by prior knowledge of the motion, that is approximate, is made by defining the function $J(\vec{g},\lambda)=\lambda S(M\vec{g})+Q(\vec{g})$. One step of the processing method comprises the determination of a sequence of images $\vec{g}^*=\{g^*(t_1),\ldots,g^*(t_N)\}$ which minimizes the function $J(\vec{g},\lambda)$ relative to $\vec{g}$ for fixed $\lambda$ and gives an approximate solution off $\vec{f}=\{f(t_1),\ldots,f(t_N)\}$, the solution to the perfectly sampled tomographic reconstruction problem. It is assumed that a convex optimization iterative algorithm is known such as those described for example in [Afonso M V, Bioucas-Dias J M, Figueiredo M A., "*Fast image recovery using variable splitting and constrained optimization,*" IEEE Trans Image Process. (9):2345-56] and [Beck A, Teboulle M. "*Fast gradient-based algorithms far constrained total variation image denoising and deblurring problems.*" IEEE Trans Image Process. 18(11):2419-34] for minimization of $J(\vec{g},\lambda)$.

The iteration is denoted $A_\lambda$ allowing the minimization of $J(\vec{g},\lambda)$ relative to $\vec{g}$ for fixed $\vec{\lambda}$ and $\vec{h}=A_\lambda^\kappa[\vec{g}]$ is the sequence of 3D images resulting from the application of $\kappa$ iteration(s) of the algorithm to the sequence of 3D images $\vec{g}$. For fixed $\vec{g}^0$, e.g. a null sequence, the algorithm is such that $$\lim_{\kappa\to\infty} A_\lambda^\kappa\left(\vec{g}^0\right) = \mathrm{argmin}_{\vec{g}} J(\vec{g},\lambda),$$

and in particular such that $$A_\lambda^\kappa\left(\vec{g}^0\right) \approx \mathrm{argmin}_{\vec{g}} J(\vec{g},\lambda)$$

for $\kappa$ finite and sufficiently small.

The reconstruction method comprises the definition of a decreasing sequence of degrees of compressibility $\Lambda=\{\lambda_1,\ldots,\lambda_\Xi\}$ such as $\lambda_1>\ldots>\lambda_\Xi\geq 0$ for which, from the arbitrary sequence $\vec{g}^0$, an estimation $\vec{g}^*(\Lambda,\vec{g}^0)$ is determined of $\vec{f}$, the solution to the perfectly sampled tomographic reconstruction problem, as follows:

$$\begin{cases} \vec{g}^0, \Lambda=\{\lambda_1,\ldots,\lambda_\Xi\} \text{ given} \\ \vec{g}(\lambda_1) = A_{\lambda_1}^\kappa\left[\vec{g}^0\right] \\ \vec{g}(\lambda_\xi) = A_{\lambda_\xi}^\kappa\left[\vec{g}(\lambda_{\xi-1})\right] \ \forall\ \xi\in\{2,\ldots,\Xi\} \\ \vec{g}^*\left(\Lambda,\vec{g}^0\right) = \vec{g}(\lambda_\Xi) \end{cases}$$

With each iteration, the algorithm allows determination of the sequence of 3D images $\vec{g}$ which, for a given value of $\lambda_\xi$, minimizes the function or $J(\vec{g},\lambda_\xi)$.

As a variant, the number of iterations $\kappa$ is preferably chosen to depend on the degree of compressibility $\lambda_\xi$ and is inversely proportional thereto.

Figure 4:
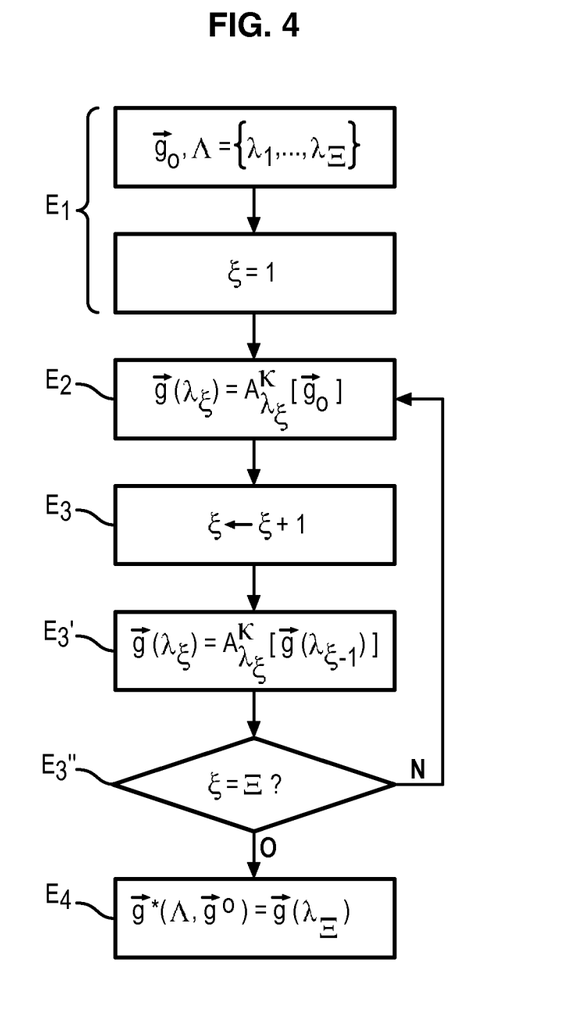
FIG. 4 schematically illustrates steps of a method according to an embodiment of the invention.

FIG. 4, diagrams the method to obtain $\vec{g}^*(\Lambda,\vec{g}^0)$, which is the approximate solution to the problem. In a first step $E_1$, $\vec{g}^0$ and $\Lambda$ are fixed. In a second step $E_2$, a sequence $\vec{g}(\lambda_1)=A_{\lambda_1}^\kappa[\vec{g}^0]$ is determined, which is the sequence that minimizes the function $J(\vec{g},\lambda_1)$ relative to $\vec{g}$ for a fixed $\lambda_1$ starting from $\vec{g}^0$. Next, iteratively, in another steps $E_3$, $E_3'$, $E_3''$ we determine $\vec{g}(\lambda_\xi)=A_{\lambda_\xi}^\kappa[\vec{g}(\lambda_{\xi-1})]\ \forall\ \xi\in\{2,\ldots,\Xi\}$ which corresponds to the sequence $\vec{g}(\lambda_\xi)$ that minimizes the function $J(\vec{g},\lambda_\xi)$ relative to $\vec{g}$ for a fixed $\lambda_\xi$ starting from $\vec{g}(\lambda_{\xi-1})$. In step $E_4$, $\vec{g}^*(\Lambda,\vec{g}^0)$ is obtained, which is the approximate solution to the problem of tomographic reconstruction. The number of approximations $\Xi$ and the number of iterations per approximation $\kappa$ are fixed such that they form the best compromise between the quality of $\vec{g}^*(\Lambda,\vec{g}^0)$ and the computing time needed to generate $\vec{g}^*(\Lambda,\vec{g}^0)$, which is proportional to both $\Xi$ and $\kappa$. The sequence of 3D images $\vec{g}^*(\Lambda,\vec{g}^0)$ therefore represents the reconstruction of the moving object.

The method for processing radiological images can advantageously be implemented in the form of a computer programme comprising machine instructions for applying the method.

What is claimed is:

1. A method for processing a sequence of sets of 2D projection images of a moving object, the motion of which is described by a set of positions referenced by $t=\{t_1,\ldots,t_N\}$, wherein the sequence of sets of 2D projection images is obtained by a medical imaging system that is in motion along a trajectory, wherein each set of 2D projection images is defined by the following equation:

$$R(t_n)f(t_n)=p(t_n),$$

where $t_n$ is the position referenced, $p(t_n)$ is a set of 2D projection images, $f(t_n)$ is the 3D image of the object at the position referenced, and $R(t_n)$ is a projection operator which models the sampling made by the medical imaging system according to its motion along its trajectory for the position referenced, wherein the method comprises:

determining a sequence of images which minimize the function:

$$J(\vec{g},\lambda)=\lambda S(M\vec{g})+Q(\vec{g})$$

where $\vec{g}$ is a set of 3D images referenced by $\vec{g}=\{g(t_1),\ldots,g(t_N)\}$, $Q(\vec{g})$ is a term of fidelity of the sequence of images, $S(\vec{g})$ is a function of spatial and temporal compression of the sequence of images, $\lambda$ is a compressibility parameter, and M is a sequence of operators for an approximate modelling of motion referenced by $M=\{M(t_1),\ldots,M(t_N)\}$, wherein the sequence of operators leads to a compression constraint augmented by partial knowledge of the motion $S(M\vec{g})$ where $M\vec{g}=\{M(t_1)g(t_1),\ldots,M(t_N)g(t_N)\}$;

wherein minimization comprises defining a decreasing sequence of degrees of compressibility for which, an estimation is determined from an initial sequence where $\vec{f}=\{f(t_1),\ldots,f(t_N)\}$ according to the following equations:

$$\begin{cases} \vec{g}^0, \Lambda=\{\lambda_1,\ldots,\lambda_\Xi\} \text{ given} \\ \vec{g}(\lambda_1) = A_{\lambda_1}^\kappa\left[\vec{g}^0\right] \\ \vec{g}(\lambda_\xi) = A_{\lambda_\xi}^\kappa\left[\vec{g}(\lambda_{\xi-1})\right] \ \forall\ \xi\in\{2,\ldots,\Xi\} \\ \vec{g}^*\left(\Lambda,\vec{g}^0\right) = \vec{g}(\lambda_\Xi) \end{cases}$$

where $\Lambda=\{\lambda_1, \ldots, \lambda_E\}$ is a decreasing sequence of degrees of compressibility $\vec{g}*(\Lambda, \vec{g}^0)$ is the estimation, $\vec{g}^0$ is the initial sequence, $A_\lambda$ is an iteration of an algorithm enabling the minimization of $J(\vec{g}, \lambda)$ relative to $\vec{g}$ for a fixed $\lambda$ and $A_\lambda^\kappa[\vec{h}]$ is a sequence of 3D images resulting from the application of $\kappa$ iterations of algorithm $A_\lambda$ to a sequence of 3D images referenced by $\vec{h}$.

2. The method according to claim 1 wherein prior knowledge of motion is such that $M(t_n)$ is the identity.

3. The method according to claim 1, wherein $Q(\vec{g})$ is a criterion of ordinary, of weighted or of filtered least-squares.

4. The method according to claim 1, wherein $S(\vec{h}) = \|\Im_t W_{xyz} \vec{h}\|_1$ where $W_{xyz}\vec{h}$ a spatial transform allowing the individual compression of each 3D image of the sequence of 3D images and where $W_{xyz}\vec{h} = \{W_{xyz}h(t_1), \ldots, W_{xyz}h(t_N)\}$, t is an axis, $\Im_t$ is a transform derived from a, Fourier analysis along the axis following the motion of the moving object and $\|\ \|_1$ symbolizes the $L_1$ norm.

5. The method according to claim, 1 wherein the initial sequence is a null sequence.

6. The method according to claim 1, wherein the sequence of sets of 2D projection images are previously acquired images stored in a storage unit of the medical imaging system.

7. A medical imaging system comprising:
an acquisition unit comprising a radiation source and a sensor, the acquisition unit configured to acquire a sequence of sets of 2D projection images $\vec{p} = \{p(t_1), \ldots, p(t_N)\}$ of a moving object while the acquisition unit is in motion along a trajectory, wherein the motion of the moving object is described by a set of positions referenced by $t = \{t_1, \ldots, t_N\}$, wherein each set of 2D projection images is defined by the following equation:

$$R(t_n)f(t_n) = p(t_n),$$

where $t_n$ is the position referenced, $p(t_n)$ is a set of 2D projection images, $f(t_n)$ is the 3D image of the object at the position referenced, and $R(t_n)$ is a projection operator which models the sampling made by the medical imaging system according to its motion along its trajectory for position of the object; and a computing unit configured to determine a sequence of images $\vec{g} = \{g*(t_1), \ldots, g*(t_N)\}$ which minimizes the function:

$$J(\vec{g}, \lambda) = \lambda S(M\vec{g}) + Q(\vec{g})$$

where $\vec{g}$ is a set of 3D images defined by $\vec{g} = \{g(t_1), \ldots, g(t_N)\}$, $Q(\vec{g})$ is a term of fidelity of the sequence of images, $S(\vec{g})$ is a function of spatial and temporal compression of the sequence of images, $\lambda$ is a compressibility parameter, and M is a sequence of operators for an approximate modelling of motion defined by $M = \{M(t_1), \ldots, M(t_N)\}$ that leads to a compression constraint augmented by partial knowledge of the motion $S(M\vec{g})$ where $M\vec{g} = \{M(t_1)g(t_1), \ldots, M(t_N)g(t_N)\}$;

wherein minimization comprises defining a decreasing sequence of degrees of compressibility for which, an estimation is determined from an initial sequence where $\vec{f} = \{f(t_1), \ldots, f(t_N)\}$ according to the following equations:

$$\begin{cases} \vec{g}^0, \Lambda = \{\lambda_1, \ldots, \lambda_\Xi\} \text{ given} \\ \vec{g}(\lambda_1) = A^\kappa_{\lambda_1}[\vec{g}^0] \\ \vec{g}(\lambda_\xi) = A^\kappa_{\lambda_\xi}[\vec{g}(\lambda_{\xi-1})] \ \forall\ \xi \in \{2, \ldots, \Xi\} \\ \vec{g}*(\Lambda, \vec{g}^0) = \vec{g}(\lambda_\Xi) \end{cases}$$

where $\Lambda = \{\lambda_1, \ldots, \lambda_E\}$ is a decreasing sequence of degrees of compressibility, $\vec{g}*(\Lambda, \vec{g}^0)$ is the estimation, $\vec{g}^0$ is the initial sequence, $A_\lambda$ is an iteration of an algorithm enabling the minimization of $J(\vec{g}, \lambda)$ relative to $\vec{g}$ for a fixed $\lambda$ and $A_\lambda^\kappa[\vec{h}]$ sequence of 3D images resulting from the application of $\kappa$ iterations of algorithm $A_\lambda$ to a sequence of 3D images referenced by $\vec{h}$.

* * * * *

UNITED STATES PATENT AND TRADEMARK OFFICE
CERTIFICATE OF CORRECTION

PATENT NO. : 8,792,700 B2
APPLICATION NO. : 13/250245
DATED : July 29, 2014
INVENTOR(S) : Riddell et al.

It is certified that error appears in the above-identified patent and that said Letters Patent is hereby corrected as shown below:

In the Specification

In Column 2, Line 6, delete "if the" and insert -- If the --, therefor.

In Column 3, Line 17, delete "Carrol" and insert -- Carrol JD, --, therefor.

In Column 3, Line 44, delete "$\vec{p} = \{p(t_1), \ldots, p(t_N)\}$," and insert -- $\vec{p} = \{p(t_1), \ldots, p(t_N)\}$ --, therefor.

In Column 4, Line 59, delete "by the)" and insert -- by the --, therefor.

In Column 7, Line 14, delete "far" and insert -- for --, therefor.

In Column 7, Line 20, delete "fixed λ" and insert -- fixed $\vec{\lambda}$ --, therefor.

In Column 7, Line 27, delete "$\lim_{K \to \infty} A_\lambda^K(\vec{g}^0) = \arg\min_{\vec{g}} J(\vec{g}, \lambda),$" and insert -- $\lim_{K \to \infty} A_\lambda^K(\vec{g}^0) = \arg\min_{\vec{g}} J(\vec{g}, \lambda),$ --, therefor.

In Column 8, Line 2, delete "$\vec{g}(\lambda_\xi) = A_{\lambda_\xi}^K[\vec{g}(\lambda_{\xi-1})] \forall \xi \in \{2, \ldots, \Xi\}$," and insert -- $\vec{g}(\lambda_\xi) = A_{\lambda_\xi}^K[\vec{g}(\lambda_{\xi-1})] \forall \xi \in \{2, \ldots, \Xi\}$, --, therefor.

Signed and Sealed this
Twenty-eighth Day of April, 2015

Michelle K. Lee
*Director of the United States Patent and Trademark Office*

CERTIFICATE OF CORRECTION (continued)
U.S. Pat. No. 8,792,700 B2

In the Claims

In Column 9, Line 2, in Claim 1, delete "compressibility" and insert -- compressibility, --, therefor.

In Column 9, Line 17, in Claim 4, delete "from a," and insert -- form a --, therefor.